United States Patent
von der Heyde et al.

(10) Patent No.: US 6,383,987 B1
(45) Date of Patent: May 7, 2002

(54) CYCLOHEXENONE OXIME ETHER/ (GLYPHOSATES/GLUPHOSINATES) SUSPENSION CONCENTRATES

(75) Inventors: Jürgen von der Heyde, Bensheim; Reiner Kober, Fussgönheim; Matthias Bratz, Limburgerhof; Rainer Berghaus, Speyer; Karl-Friedrich Jäger, Limburgerhof; Jürgen Fries, Ludwigshafen; Adolf Parg, Bad Dürkheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/868,072
(22) PCT Filed: Dec. 15, 1999
(86) PCT No.: PCT/EP99/09956
§ 371 Date: Aug. 2, 2001
§ 102(e) Date: Aug. 2, 2001
(87) PCT Pub. No.: WO00/35288
PCT Pub. Date: Jun. 22, 2000
(51) Int. Cl.$^7$ .......................... A01N 43/80; A01N 43/56
(52) U.S. Cl. ...................... 504/271; 504/280; 504/288; 504/291
(58) Field of Search ................................ 504/271, 280, 504/288, 291

(56) References Cited

U.S. PATENT DOCUMENTS

| | | | |
|---|---|---|---|
| 5,886,233 A | * 3/1999 | Steinmeyer et al. | 568/376 |
| 5,981,440 A | * 11/1999 | Bratz et al. | 504/344 |
| 6,039,966 A | * 3/2000 | Kostka et al. | 424/405 |
| 6,133,202 A | * 10/2000 | Bratz et al. | 503/244 |

* cited by examiner

*Primary Examiner*—Deborah C. Lambkin
(74) *Attorney, Agent, or Firm*—Keil & Weinkauf

(57) ABSTRACT

A substantially water-free formulation of crop protection agents, comprising essentially a) a cyclohexenone oxime ether of the formula I

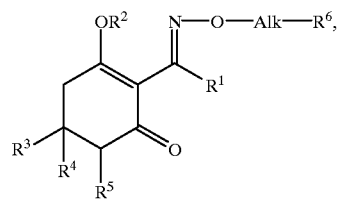

where
$R^1$=ethyl, propyl;
$R^2$=hydrogen or an equivalent of an agriculturally useful cation;
$R^3$=2-(thioethyl)propyl, tetrahydrothiopyran-3-yl, tetrahydrothiopyran-4-yl, tetrahydropyran-3-yl, tetrahydropyran-4-yl, 1-(methylthio)cyclopropyl, 5-(isopropyl)isoxazol-3-yl, 2,5-dimethylpyrazol-3-yl, 2,4,6-trimethylphenyl or 2,4,6-trimethyl-3-butyrylphenyl;
$R^4$, $R^5$=H, $CH_3$, CO—$OCH_3$;
Alk=$CH_2CH_2$, $CH_2CH(CH_3)$, $CH_2CH$=CH, $CH_2CH$=C(Cl), $CH_2CH_2CH$=CH;
$R^6$=H, phenyl, halophenyl, dihalophenyl, phenoxy, halophenoxy, dihalophenoxy;

b) N-phosphonamethylglycine, or an ester or salt thereof, DL-homoalanin-4-yl(methyl)phosphinic acid or its ammonium salt;

c) from 20 to 80% by weight of an aprotic or weakly protic solvent in which the components a) and b) are suspended;

d) if desired emulsifiers, surfactants, surface-active and/or activity-enhancing auxiliaries, is described.

10 Claims, No Drawings

CYCLOHEXENONE OXIME ETHER/ (GLYPHOSATES/GLUPHOSINATES) SUSPENSION CONCENTRATES

This appln is a 371 of PCT/EP99/09956 Dec. 15, 1999.

The present invention relates to a novel substantially water-free formulation of crop protection agents, comprising essentially a) cyclohexenone oxime ether of the formula I

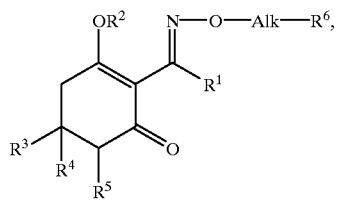

where the variables are defined as follows:
$R^1$ is ethyl or propyl;
$R^2$ is hydrogen or an equivalent of an agriculturally useful cation;
$R^3$ is 2-(thioethyl)propyl, tetrahydrathiopyran-3-yl, tetrahydrothiopyran-4-yl, tetrahydropyran-3-yl, tetrahydropyran-4-yl, 1-(methylthio)cyclopropyl, 5-(isopropyl)isoxazol-3-yl, 2,5-dimethylpyrazol-3-yl, 2,4,6-trimethylphenyl or 2,4,6-trimethyl-3-butyrylphenyl;
$R^4$ and $R^5$ independently of one another are each hydrogen, methyl or methoxycarbonyl;
Alk is $CH_2CH_2$, $CH_2CH(CH_3)$, $CH_2CH=CH$, $CH_2CH=C(Cl)$ or $CH_2CH_2CH=CH$;
$R^6$ is hydrogen, phenyl, halophenyl, dihalophenyl, phenoxy, halophenoxy or dihalophenoxy;

b) N-phosphonamethylglycine (glyphosate), an ester or salt thereof, DL-homoalanin-4-yl(methyl)phosphinic acid (glufosinate) or its ammonium salt:

c) from 20 to 80% by weight of an aprotic or weakly protic solvent in which the components a) and b) are dissolved or suspended;

d) if desired emulsifiers, surfactants, surface-active and/or activity-enhancing auxiliaries.

Moreover, the invention relates to processes for preparing a spray liquor for controlling undesirable plants.

It is known that herbicides from the substance class of the cyclohexenone oxime ethers have the tendency to undergo hydrolytic decomposition or chemical degradation reactions in aqueous or protic solvents. For this reason, cyclohexenone oxime ethers have hitherto only been prepared and employed as water-free emulsion concentrates.

A possible alternative is offered by formulations of solids, as described in WO 96/29869.

However, formulations of solids have the disadvantage that it is either not possible or possible only in very small amounts to incorporate activity-enhancing additives, for example lipophilic esters, such as methyl oleate, lauric and adipic esters, as well as paraffin oil or fatty acid esters, if appropriate in combination with selected emulsifiers However, mixtures of the cyclohexenone oxime ethers I and glyphosate, glufosinate or a derivative thereof would allow better control of undesirable grasses than glyphosate/glufosinate on its own. It is even an essential precondition for the economical control of "Round up Ready", self-sown maize in "Round up Ready" soya beans. This generally applies to grasses which are resistant (tolerant) to glyphosate.

It is an object of the present invention to provide a liquid finished formulation which comprises a cyclohexenone oxime ether herbicide, N-phosphonomethylglycine or a derivative thereof and, if desired, an activity-enhancing auxiliary and is sufficiently storage-stable.

We have found that this object is achieved by the suspension concentrates defined at the outset. Furthermore, we have found a process for preparing a herbicidally active spray liquor.

The present suspension concentrates are characterized by the fact that the proportion of free water (which is not bound as water of crystallization) is from 0 to 5% by weight, preferably from 0 to 2% by weight and in particular only from 0 to 0.5% by weight.

Preferred herbicide components a) are cyclohexenone oxime ethers selected from the group consisting of: sethoxydim, cycloxydim, clethodim, tralkoxydim, butroxydim, 2-(1-(3-chloroallyloxy)iminopropyl)-5-(tetrahydropyran-4-yl)-3-hydroxycyclohex-2-enone, 2-[1-(2-p-chlorophenoxypropyloxy)iminobutyl]-5-(tetrahydrothiopyran-3-yl)-3-hydroxycyclohex-2-enone or mixtures thereof, in particular clethodim or 2-(1-(3-chloroallyloxy)iminopropyl)-5-(tetrahydropyran-4-yl)-3-hydroxycyclohex-2-enone. These active ingredients are usually soluble in the oil phase. Also suitable, however, are the alkali metal or alkaline earth metal salts of the preferably or particularly mentioned cyclohexanone oxime ethers, which, in combination with selected assistants, are substantially insoluble in the continuous oil phase, with the result that the degradation of the active ingredients I is substantially prevented. Thus, preferred cyclohexanone oxime ether salts are those which are present in solution in the oil phase and in an amount of <1%, very particularly preferably <0.1–0.5%.

The salts of the cyclohexenone oxime ethers I are generally obtainable by reacting the free compounds I ($R^2$= hydrogen) with basic metal salt solutions. Suitable sources of basic metal salts are typically hydroxides, carbonates or phosphates of alkali metals, alkaline earth metals or transition metals. Cations of a higher valence, such as calcium and magnesium, which were employed in approximately equimolar amounts to the compounds I, may additionally, for charge neutralization, be associated with anions of mineral acids or organic acids. By spray drying of the aqueous solution of a potassium or a calcium salt, it is then possible to prepare granules which contain approximately 100% by weight of cyclohexenone oxime ether metal salt.

The component b) consists of known commercial products. The common names are glyphosate, sulfosate and glufosinate, and the corresponding trademarks are RoundUp®, Touchdown® and Basta® respectively.

In the context of the present invention, particular preference is given to mixtures which comprise, as derivative of N-phosphonomethylglycine, the isopropylammonium salt of N-phosphonomethylglycine which is known as glyphosate. Other known derivatives of phosphonomethylglycine are the trimethylsulfonium salt, which is known under the name sulfosate, and the ammonium salt. However, particular preference is given to the product mentioned at the outset, which is known as glyphosate, in particular its ammonium salt.

A mono-, di- or trideprotonated salt of glyphosate, in particular alkali metal, alkaline earth metal, transition metal or ammonium salts, has been found to be a useful herbicide component b). The ammonium salt of glyphosate is very particularly preferred.

In general, an excess of component b) is employed, up to approximately 10 times the molar amount, in particular approximately 7 to 8 times the molar amount, based on the amount of component a).

Suitable aprotic or weakly protic solvents which serve as component c) are nonpolar, polar or dipolar aliphatic or aromatic solvents which exhibit only low solubilizing power, if any at all, toward the component b). To obtain storage-stable formulations, the solubility of the active compound b) in the oil phase should be below it by weight (based on the total formulation). This also applies to component a), as long as the salts of the compounds I are used. Preference is given to hydrocarbons, such as benzene, alkylbenzene and naphthalene, and their mono- and polyalkyl-substituted and/ or partially hydrogenated derivatives, n- or isoparaffins having 8 to 30 carbon atoms, aliphatic or aromatic esters of mono- or dicarboxylic acids, such as methyl oleate, octyl laurate and octyl adipate and benzoic esters, or to unmodified or modified natural fats and oils, such as soya oil, sunflower oil and rapeseed oil methyl ester.

Particular preference is given to aromatic solvents of the benzene and naphthalene series, such as Solvesso® 150 and Solvesso® 200 (alkylaromatics from Exxon).

In addition to the component c), the formulations according to the invention generally comprise emulsifiers, surfactants and surface-active auxiliaries such as wetting agents and dispersants as further components.

Suitable surfactants, wetting agents and dispersants are, for example:
1. anionic surfactants and dispersants, especially
   soaps (alkali metal, alkaline earth metal or ammonium salts of fatty acids), for example potassium stearate;
   alkyl sulfates;
   alkyl ether sulfates, for example sulfated hexa-, hepta- and octadecanols and fatty alcohol glycol ethers;
   alkyl- or isoalkylsulfonates;
   alkali metal, alkaline earth metal or ammonium salts of arylsulfonic acids or alkylbenzenesulfonic acids, for example ligno-, phenolsulfonic acids, naphthalene- and dibutylnaphthalenesulfonic acids or Na-dodecylbenzenesulfonates;
   alkylnaphthalenesulfonates;
   alkyl methyl ester sulfonates;
   acyl glutamates;
   sulfonate esters of alkylsuccinic acid;
   alkyl mono/diphosphates;
   sarcosinates, for example Na-lauroyl sarcosinate;
   taurates;
   condensates of sulfonated naphthalene and its derivatives with formaldehyde;
   condensates of naphthalenesulfonic acids, phenol- and/ or phenolsulfonic acids, formaldehyde and urea,
   protein hydrolysates;
   lignosulfite waste liquors and methylcellulose, where these substances act in particular as dispersants;
   Aerosol® OT-A;
2. Cationic surfactants:
   alkyltrimethylammonium halides/alkyl sulfates;
   alkylpyridinium halides;
   dialkyldimethylammonium halides/alkyl sulfates;
3. Nonionic surfactants:
   fatty acid polyoxyethylene esters, such as lauryl alcohol polyoxyethylene ether acetate;
   alkyl polyoxyethylene ethers or polyoxypropylene ethers, for example of isotridecyl alcohol, and fatty alcohol polyoxyethylene ethers;
   alkylaryl alcohol polyoxyethylene ethers, such as octylphenol polyoxyethylene ethers;
   alkoxylated animal/vegetable fats or oils, such as maize oil ethoxylates, castor oil ethoxylates and tallow fat ethoxylates;
   glycerol esters, such as glycerol monostearate;
   fatty alcohol alkoxylates or oxoalcohol alkoxylates;
   fatty acid alkoxylates, such as oleic acid ethoxylates;
   alkylphenol alkoxylates, such as ethoxylated iso-octyl-, octyl- or nonylphenol, and tributylphenol polyoxyethylene ether;
   fatty amine alkoxylates;
   fatty acid amide alkoxylates;
   sugar surfactants, sorbitol esters such as sorbitan fatty acid ester (sorbitan monooleate, sorbitan tristearate), polyoxyethylene sorbitan fatty acid esters, alkylpolyglycosides and N-alkylgluconamides;
   alkylmethyl sulfoxides;
   alkyldimethylphosphine oxides, such as tetradecyldimethylphosphine oxide;
   polyoxyethylene sugar alcohol fatty alkylcarboxylates such as polyoxyethylene-(40)-sorbitolhexaoleate Atlas G 1086 (CAS No. 057171-56-9) from ICI surfactants;
4. Zwitterionic surfactants:
   sulfobetaines;
   carboxybetaines;
   alkyldimethylamine oxides, such as tetradecyldimethylamine oxide;
5. Polymer surfactants:
   di-, tri- and multi-block polymers of the type $(AB)_x$, ABA and BAB, for example polyethylene oxide block polypropylene oxide or polystyrene block polyethylene oxide;
   AB comb polymers, for example polymeth/acrylate comb polyethylene oxide;
6. Other surfactants, for example
   perfluoro surfactants;
   silicone surfactants;
   phospholipids, such as lecithin or chemically modified lecithins;
   amino acid surfactants, such as N-lauroyl glutamate;
   surface-active homo- and copolymers, such as polyvinylpyrrolidone, polyacrylic acid, polyvinyl alcohol, polyethylene oxide, maleic anhydride/ isobutene copolymrs and vinylpyrrolidone/vinyl acetate copolymers.

Mixtures of the abovementioned surfactants are also suitable. The nonionic surfactants from the group consisting of the polyoxyethylene sugar alcohol fatty alkylcarboxylates, e.g. polyoxyethylene-(40)-sorbitolhexaoleate Atlas G 1086 (CAS No. 057171-56-9) from ICI Surfactants, and ionic surfactants from the alkali metal and alkaline earth metal alkyl, dialkyl- or alkylarylsulfonate series are particularly suitable. Emulsifiers and surfactants which were obtained by reacting a natural oil, in particular castor oil, with ethylene oxide or propylene oxide are furthermore advantageous (in this context, cf. for example statements in DE-A 19 701 123).

The alkyl chains of the abovementioned surfactants, wetting agents and dispersants may be linear or branched, and the length of the alkyl chains is generally from $C_8$ to $C_{20}$.

To improve the physical properties with respect to reduced formation of serum or reduced sedimentation, the formulations according to the invention may furthermore comprise thickeners, which are generally understood to be mineral components, such as bentonites, talicites and hectorites or castor oil derivatives. Owing to the resulting increase in viscosity, chemical processes which occur on storage in the formulations are, if appropriate, suppressed, which may lead to improved stability of the active compound.

With regard to activity-enhancing auxiliaries, such as adipic esters, methyl oleate and other industrial esters based on natural carboxylic acids, dicarboxylic acids or fatty acids, reference is made to WO 96/22020, DE-A 44 45 546 and the literature cited therein.

All of the abovementioned auxiliaries can be added to the formulation batch before or after grinding. The total proportion of auxiliaries in the formulation is generally from 0 to 80% by weight and in particular from 5 to 40% by weight.

If desired, the formulations may also comprise from 0 to 60% by weight, in particular from 1 to 30% by weight, of a third herbicidally active compound selected from the group consisting of the aryloxyphenoxypropionic acids and their esters, preferably clodinafop, cyhalofop, fenoxaprop, fluazifop, haloxyfop, propaquizafop, quizalofop or an ester of these compounds in particular clodinafop, quizalofop, quizalofop-ethyl or quizalofop-tefuryl.

The enantiomers of these compounds, such as quizalofop-P, quizalofop-P-ethyl and quizalofop-P-tefuryl are also suitable.

The novel formulations according to the invention are advantageously first diluted with water, for example in the tankmix method, before they are applied to the undesirable plants or their habitat by the pre-emergence or post-emergence method. Here, the amount of water is, for example, from 100 to 400 l/ha.

To lower the pH of the tankmix and to further enhance the activity, it may also be advantageous to add customary tankmix adjuvants in an amount of from 0.1 to 5.0 kg/ha or 0.1 to 5.0 l/ha, for example ammonium salts, such as ammonium sulfate and ammonium nitrate urea, oil emulsifier additives and in particular Dash RC (from BASF).

The suspension concentrates according to the invention are prepared by intensively grinding the active compounds a) and b) in crystalline form and the component c) and, if desired, auxiliaries and/or other herbicidally active compounds using customary ball mills, bead mills or stirrer mills.

Suitable for use as grinding medium are, for example, glass grinding media or other mineral or metallic grinding media having a size of from 0.1 to 30 mm, preferably from 0.6 to 2 mm, and the suspensions are generally comminuted until the average particle size is considerably less than 10 $\mu$m.

It is particularly advantageous here that the fine-particulate active compounds in their salt form dissolve quantitatively when diluted with water in the tankmix. As a consequence, the active compound is available to the plant in homogeneous and virtually monomolecular form, owing to which particularly favorable herbicidal properties are in general achieved.

High proportions of lipophilic auxiliaries and bipolar surfactants advantageously support penetration or transduction/transmision of the active compounds in the leaves. Such auxiliaries are native fats and oils and, in particular, their fatty acid methyl esters, for example methyl oleate.

The present substantially water-free formulations furthermore make an application by the ULV method (ultra light application) possible where, for example for application by plane, the formulation can be mixed or diluted directly with a water-free oil concentrate (for example Spraytex-Öl a product from Exxon) at approximately 10–50 l per hectare with generally good compatibility.

The formulations according to the invention have excellent activity against a broad spectrum of undesirable harmful plants.

In addition, they are also particularly preferably suitable for use in controlling undesirable vegetation in crops in which the crop plants have been provided, by suitable modification, with an increased resistance toward N-phosphonomethylglycine, which per se acts as a total herbicide.

The formulations according to the invention are used as herbicides. The corresponding herbicidal compositions control vegetation on areas which are not under cultivation very efficiently, in particular at high application rates. In genetically modified dicotyledonous crops having increased resistance against glyphosate or glufosinate such as in soybeans, rape, sugar beet, flax, peas, potatoes, lentils and cotton, they act against weeds and harmful grasses without significantly damaging the crop plants. This effect is already observed at low application rates.

The formulations according to the invention are particularly useful for controlling undesirable vegetation in soya bean crops, in which the soya plants themselves are resistant toward N-phosphonomethylglycine and its esters or salts. It has been found to be particularly advantageous in this context that it is possible to selectively control undesirable maize plants which may occur in soya bean crops owing to the annual crop rotation between soya beans and maize (so-called "volunteer corn").

Depending on the method of application in question, the formulations according to the invention or the spray liquors prepared from them can be employed in a number of other modified crop plants for eliminating undesirable plants. Suitable crops are, for example:

*Allium cepa, Ananas comosus, Arachis hypogaea, Asparagus officinalis, Beta vulgaris* spec., *altissima, Beta vulgaris* spec., *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Bordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum* (*N.rustica*), *Olea europaea, Oryza sativa, Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays.*

The mixtures or the herbicidal compositions can be applied by the pre-emergence or by the post-emergence method. If the active compounds are less well tolerated by certain crop plants, application techniques can be used in which the herbicidal compositions are sprayed, with the aid of the spraying equipment, in such a way that they come into as little contact as possible, if any, with the leaves of the sensitive crop plants while the active compounds reach the leaves of undesirable plants growing underneath, or the naked soil surface (post-directed, lay by).

The application rates of the finished spray liquor are from 0.001 to 3.0, preferably from 0.01 to 2.0, kg/ha of active substances (a.s.), depending on the intended target, the season, the target plants and the growth stage.

Moreover, it may be useful to apply the finished spray liquor not only in combination with other herbicides but also with other crop protection agents, for example with agents for controlling pests or phytopathogenic fungi or bacteria. Also of interest is the miscibility with mineral salt solutions which are employed for overcoming a lack of nutrients and trace elements. It is also possible to add nonphytotoxic oils and oil, concentrates.

Undesirable vegetation is controlled by allowing a herbicidally effective amount of a crop protection agent formulation based on the formulation of the present invention to act on the crop plant, its habitat and/or its seeds.

PREPARATION EXAMPLES

Example 1

Using 0.9–1.2 mm glass beads as grinding medium, the active compounds of the components a) and b) were ground, generally at approximately 0–30° C., with the component c) and, if desired, other formulation auxiliaries and/or herbicidally active compounds.

When the cyclohexanone oxime ethers I were used in the form of free acids, it was advisable not to add them until or after component b) had been milled.

The concentration of active compound was in total approximately 10–60%, generally 30–60%.

Grinding was carried out in a Dynomill from Bachofen using a batch size of from 0.5 to one liter, in passage operation. In general after 5 passages (pumping of the slurry through the mill using a peristaltic pump) average particle sizes of 1–10 μm were achieved according to microscopic evaluation. Incorporation and dilution with other auxiliaries and, if appropriate, an active ingredient I (as free acid) were subsequently carried out by homogenizing for 10 min using a KPG stirrer or a magnetic stirrer.

Example 2

Starting materials (general basic formulation):

240–550 g/l of glyphosate (calculated relative to pure active ingredient fraction)

10–80 g/l of cyclohexenone oxime ether

100–350 g/l of emulsifier(s)

aprotic diluents/solvents to 1 l.

According to the abovementioned basic formulation, glyphosate—as free compound or as salt—was mixed with the emulsifiers to 0.9 l volume, per l of oil SC:

The components were prehomogenized by stirring for 1–2 minutes and were milled by means of a glass bead mill or Dynomill via a peristaltic pump.

Depending on the characteristics or depending on the crystal size of the active ingredient glyphosate, it was necessary to comminute the dry active ingredient beforehand, for example by means of a pinned disk mill.

Milling parameters:

Milling container volume 0.5 l, glass bead load about 80%[1], glass beads 1.0–1.4 mm diameter; 5 passages batchwise; cooling of the mill with water (10° C. inlet temperature and about 20° outlet temperature).

[1] i.e. mill filled to 80% by volume with glass beads

Typical particle sizes: 0.1 to 10 μm after milling, including in particular 30–80% <2 μm.

Homogeneous, in some cases slightly viscous oil SCs or glyphosate oil SC preconcentrates were obtained. The intended amounts of cyclohexenone oxime ether I—if necessary as dilute preconcentrates—were then stirred into the glyphosate oil SC at about 20° C. (about 30 minutes by means of a dissolver at 800 U/min). Finally, the mixture was made up to 1.0 l with solvent or diluent.

When all active ingredients (i.e. I and glyphosate/glufosinate) are used in salt form, it may be advantageous first to prepare separate oil suspension concentrates of components a) and b) (master SCs).

Example 3

Shelf Life

The preparation of the glyphosate salts was carried out in a manner known per se by mixing or homogenizing the corresponding metal hydroxides or carbonates and glyphosate, evaporating down under reduced pressure and drying in a drying oven at a reduced pressure of 10–50 mbar overnight, after which the residual moisture contents (water content) were less than 0.5%. The stated amounts of glyphosate salts are calculated relative to the pure active ingredient.

The stability data are given only for the cyclohexenone oxime ether, since glyphosate and its salts generally do not undergo any active ingredient degradation in the novel mixture.

The cyclohexenone oxime ether I used was 2-[1-(3-chloroallyloxy)iminopropyl]-5-(tetrahydropyran-4-yl)-3-hydrozycyclohex-2-enone.

TABLE 1

| Experiment No. | Glyphosate/salt type[2] | g/l | Cyclohexenone oxime ether/type | g/l | Assistant: | g/l/ | Stability (rel. in %) after storage for 2 weeks at 54° C. |
|---|---|---|---|---|---|---|---|
| 1 | Dilithium | 266 | free compound | 33 | Atlas ® G 1086 | 150 | 93 |
|   |   |   |   |   | liquid paraffin | to 1 l |   |
| 2 | Calcium | 400 | Li salt[3] | 50 | Atlas ® G 1086 | 202 | 88 |
|   |   |   |   |   | Solvesso 200 | to 1 l |   |
| 3 | NH$_4^+$ | 266 | free compound | 34 | Atlas ® G 1049 | 150 | 96–99[4] |
|   |   |   |   |   | Solvesso 200 | to 1 l |   |
| 4 | NH$_4^+$ | 480 | free compound | 43 | Aerosol ® OT-A | 50 | 97 |
|   |   |   |   |   | Lutensol ® ON 110 | 100 |   |
|   |   |   |   |   | Sokalan ® HP 50 | 10 |   |

TABLE 1-continued

| Experiment No. | Glyphosate/ salt type[2] | g/l | Cyclo- hexenone oxime ether/type | g/l | Assistant: | g/l/ | Stability (rel. in %) after storage for 2 weeks at 54° C. |
|---|---|---|---|---|---|---|---|
| 5 | Monolithium | 266 | free compound | 33 | Atlas ® G 1086 C14–C17 liquid paraffin | 150 to 1 l | 66 |

[2] calculated relative to pure active ingredient glyphosate (acid form);
[3] after serum analysis, the Li salt was converted into the mixed Ca—Li glyphosate salt by the glyphosate Ca salt, owing to the residual acidity of the tribasic acid glyphosate in the formulation;
[4] values from two experiments.

Explanations Relating to the Assistants:

Atlas G 1086 is a polyoxyethylene-(40)-sorbitolhexaoleate (CAS No. 057171-56-9); product from Uniqema, formerly ICI Surfactants;

Solvesso 200 is an alkyl-substituted C10-aromatic; product of Exxon;

Aerosol OT-A is a sodium dioctyl sulfosuccinate (CAS No. 000577-11-7); product of Cytec;

Lutensol ON 110 is ethoxylated isodecanol; product of BASF AG;

Sokalan HP 50 is a polyvinylpyrrolidone; product of BASF AG;

Example 4

Comparative Experiments

In the comparative experiments, 2-[1-(3-chloroallyloxy) iminopropyl)-5-(tetrahydropyran-4-yl-3-hydroxycyclohex-2-enone[5]) was incorporated, with the assistants stated is Table 2, by stirring, into the commercial product Roundup® Ultra (product and label of Monsanto). The glyphosate content of the formulations obtained was then 25% by weight in each case. After storage for 2 weeks, the amount of the abovementioned cyclohexenone oxime ether as still present was tested.

where the variables are defined as follows:

$R^1$ is ethyl or propyl;

$R^2$ is hydrogen or an equivalent of an agriculturally useful cation;

$R^3$ is 2-(thioethyl)propyl, tetrahydrothiopyran-3-yl, tetrahydrothiopyran-4-yl tetrahydropyran-3-yl, tetrahydropyran-4-yl, 1-methylthio)cyclopropyl, 5-(isopropyl)isoxazol-3-yl, 2,5-dimethylpyrazol-3-yl, 2,4,6-trimethylphenyl or 2,4,6-trimethyl-3-butyrylphenyl;

$R^4$ and $R^5$ independently of one another are each hydrogen methyl or methoxycarbonyl;

Alk is $CH_2CH_2$, $CH_2CH(CH_3)$, $CH_2CH=CH$, $CH_2CH=C(Cl)$ or $CH_2CH_2CH=CH$;

$R^6$ is hydrogen, phenyl, halophenyl, dihalophenyl, phenoxy, halophenoxy or dihalophenoxy;

TABLE 2

| Experiment No. | Glyphosate salt type | %[6] | g/l Cyclo[5] | Assistant: | g/l | Stability (rel. in %) after storage for 2 weeks at 54° C. |
|---|---|---|---|---|---|---|
| 6 | Isopropylammonium | 25 | 32 | Aerosol ® OT-A Lutensol ® ON 110 Solvesso ® 200 (to 1 l) | 50 200 179 | 54.2[7] |
| 7 | Isopropylammonium | 25 | 32 | Aerosol ® OT-A Lutensol ® ON 110 water | 50 200 to 1 l | <<0.5%[8] |

[6] based on active ingredient glyphosate;
[7] 2-phase system after prolonged standing, but can be easily rehomogenized by shaking;
[8] active ingredient degradation >99%; single-phase homogeneous formulation.

The experiments of Examples 3 and 4 demonstrate that the cyclohexenone oxime ethers I can surprisingly be formulated as stable novel oil SC formulations.

What is claimed is:

1. A substantially water-free formulation of crop protection agents, comprising essentially a) at least one cyclohexenone oxime ether of the formula I b) N-Phosphomethylglycine, an ester or salt thereof, DL-homoalanin-4-yl(methyl)phosphinic acid or its ammonium salt;

c) from 20 to 80% by weight of an aprotic or weakly protic solvent in which the components a) and b) are dissolved or suspended;

d) if desired emulsifiers, surfactants, surface-active and/or activity-enhancing auxiliaries.

2. A substantially water-free formulation according to claim 1, comprising as component a) a cyclohexenone oxime ether selected from the group consisting of: sethoxydim, cycloxydim, clethodim, tralkoxydim, butroxydim, 2-[1-(3-chloroallyloxy)iminopropyl]-5-(tetrahydropyran-4-yl)-3-hydroxycyclohex-2-enone, 2-[1-(2-p-chlorophenoxypropyloxy)iminobutyl]-5-(tetrahydro-thiopyran-3-yl)-3-hydroxycyclohex-2-enone, their alkali metal or alkaline earth metal salts or mixtures of these active ingredients.

3. A substantially water-free formulation according to claim 1, comprising as component b) a mono-, di- or trideprotonated salt of glyphosate.

4. A substantially water-free formulation according to claim 1, comprising additionally from 0 to 80% by weight of at least one formulation auxiliary selected from the classes of the surface-active ionic or nonionic surfactants, dispersants, other solvents and thickeners.

5. A substantially water-free formulation according to claim 1, comprising additionally from 0 to 60% by weight of a third herbicidally active compound selected from the group consisting of the aryloxyphenoxypropionic acids and their esters.

6. A process for preparing a spray liquor for controlling undesirable plants, which comprises mixing a formulation as claimed in claim 1 with ammonium salts, water and, if desired, other tankmix adjuvants.

7. A 2-[1-(3-chloroallyloxy)iminopropyl]-5-(tetrahydropyran-4-yl)-3-hydroxycyclohex-2-enone lithium salt.

8. An oil suspension concentrate, comprising essentially
   a) at least one cyclohexenone oxime ether salt of the formula I

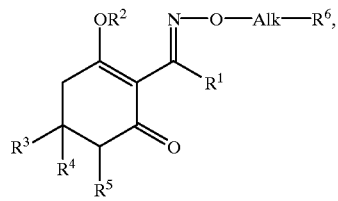

where the variable are defined as follows:
$R^1$ is ethyl or propyl;
$R^2$ is an equivalent of an agriculturally useful cation;
$R^3$ is 2-(thioethyl)propyl, tetrahydrothiopyran-3-yl, tetrahydrothiopyran-4-yl, tetrahydropyran-3-yl, tetrahydropyran-4-yl, 1-(methylthio)cyclopropyl, 5-(isopropyl)isoxazol-3-yl, 2,5-dimethylpyrazol-3-yl, 2,4,6-trimethylphenyl or 2,4,6-trimethyl-3-butyrylphenyl;
$R^4$ and $R^5$ independently of one another are each hydrogen, methyl or methoxycarbonyl;
Alk is, $CH_2CH_2$, $CH_2CH(CH_3)$, $CH_2CH=CH$, $CH_2CH=C(Cl)$ or $CH_2CH_2CH=CH$;
$R^6$ is hydrogen, phenyl, halophenyl, dihalophenyl, phenoxy halophenoxy or dihalophenoxy;
c) from 20 to 80% by weight of an aprotic or weakly protic solvent in which the component a) is suspended;
d) if desired emulsifiers, surfactants, surface-active and/or activity-enhancing auxiliaries.

9. The oil suspension concentrate according to claim 8, comprising as component
   a) at least one cyclohexenone oxime ehter salt of the formula I, where $R^2$ is an equivalent of an alkali metal or alkaline earth metal cation.

10. The oil suspension concentrate according to claim 9, where the cyclohexenone oxime ether salt is present in solution in the oil phase in an amount of less than 1%.

* * * * *

UNITED STATES PATENT AND TRADEMARK OFFICE
CERTIFICATE OF CORRECTION

PATENT NO.    : 6,383,987 B1                                         Page 1 of 1
DATED         : May 7, 2002
INVENTOR(S)   : Von Der Heyde et al.

It is certified that error appears in the above-identified patent and that said Letters Patent is hereby corrected as shown below:

Column 1,
Line 24, "Tetrahydrathiopyran" should be -- Tetrahydrothiopyran --.
Line 36, "N-phosphonamethylglycine" should be -- phosphonomethylglycine --.
Line 59, insert a period -- . -- after "emulsifiers".

Column 2,
Line 30, "cyclohexanone" should be -- cyclohexenone --.

Column 7,
Line 22, "cyclohexanone" should be -- cyclohexenone --.

Column 8,
Line 47, "hydrozycyclohex" should be -- hydroxycyclohex --.

Column 10,
Line 32, "1-methylthio)" should be -- 1-(methylthio) --.
Line 61, "N-Phosphomethylgycine" should be -- N-Phosphonomethylglycine --.

Column 12,
Line 21, "ehter" should be -- ether --.

Signed and Sealed this

Fifteenth Day of October, 2002

Attest:

Attesting Officer

JAMES E. ROGAN
Director of the United States Patent and Trademark Office